United States Patent [19]

Morcos et al.

[11] Patent Number: 5,163,898
[45] Date of Patent: Nov. 17, 1992

[54] MEDICAL TREATMENT OF TUMORS WITH PHYCOCYANIN

[75] Inventors: N. Charle Morcos, Irvine; Walter L. Henry, So. Laguna, both of Calif.

[73] Assignee: The Regents of the University of California, Oakland, Calif.

[21] Appl. No.: 635,277

[22] Filed: Dec. 28, 1990

Related U.S. Application Data

[60] Continuation-in-part of Ser. No. 373,199, Jun. 29, 1989, abandoned, which is a division of Ser. No. 25,987, Mar. 16, 1987, Pat. No. 4,886,831.

[51] Int. Cl.$^5$ .............................................. A61N 1/30
[52] U.S. Cl. .......................................... 604/20; 604/49; 514/456; 530/370
[58] Field of Search ............. 604/20, 21, 49, 53; 514/456, 2, 824; 530/370

[56] References Cited

U.S. PATENT DOCUMENTS

| | | | |
|---|---|---|---|
| 4,336,809 | 6/1982 | Clark | 606/15 |
| 4,512,762 | 4/1985 | Spears | 604/21 |
| 4,886,831 | 12/1989 | Morcos et al. | 604/21 |

Primary Examiner—Stephen C. Pellegrino
Assistant Examiner—Mchael Rafa
Attorney, Agent, or Firm—Brown, Martin, Haller & McClain

[57] ABSTRACT

A photochemical method is described for treating cancer wherein phycocyanin is administered to a patient suffering from internal or skin cancer. Once administered, phycocyanin is selectively taken up into cancer cells, and upon subsequent irradiation destruction of the cancer cells occurs. Phycocyanin offers several advantages over prior art chemicals used for similar purposes. First, it is only marginally sensitive to the ultraviolet portion of the spectrum; consequently patients can be irradiated without concern that they will be sensitized to subsequent exposure to sunlight. Second, phycocyanin is selectively taken up into cancer cells with little or no uptake by surrounding normal cells. This ensures that upon subsequent irradiation that the tumors are selectively destroyed with little or no damage to the surrounding cells or tissue. A variety of different types of cancer cells can be effectively treated by this method; treatments of breast cancer, leukemia and murine tumors are described.

24 Claims, 2 Drawing Sheets

MEDICAL TREATMENT OF TUMORS WITH PHYCOCYANIN

CROSS-REFERENCE TO RELATED APPLICATIONS

This application is a continuation-in-part of application Ser. No. 07/373,199, filed Jun. 29, 1989 abn. which in turn is a division of application Ser. No. 07/025,987, filed Mar. 16, 1987, now U.S. Pat. No. 4,886,831, issued Dec. 12, 1989.

BACKGROUND OF THE INVENTION

A variety of medical diseases are beneficially treated by therapeutic agents which are selectively directed to the site of the disease, thereby causing the death of the cells responsible for the disease without harming normal cells. Thus, there is considerable emphasis in the medical technology community focused on obtaining such site directed therapeutic chemicals. Two such diseases where these types of chemicals could be most advantageously applied are atherosclerosis and cancer. We have dealt with atherosclerosis in our above-cited U.S. Pat. No. 4,886,831, but since aspects of the atherosclerosis are applicable to the invention described and claimed herein, these will be discussed below.

Atherosclerosis is a disease associated with occlusion of blood vessels arteries and the like in which fatty substances, particularly lipids, form deposits in the vessels. Such deposits are commonly referred to as "atherosclerotic plaques". Generally, these plaques form as a result of lipids being deposited in and beneath the intima (innermost membrane lining) of arteries and veins. Generally, atherosclerosis involves medium and large-size vessels, with the most commonly affected being the aorta, iliac, femoral, coronary and cerebral arteries. If the disease is not checked, tissues or organs that are distal to the atherosclerotic plaque experience reduced blood flow and thus are adversely affected.

For the most part, atherosclerosis is treated by one of three approaches. First, the vascular regions that are diseased are often replaced by prosthetic or natural grafts. Grafting is a very expensive and medically demanding procedure, and often presents significant associated risks to the patient. The second approach is to put the atherosclerotic patient on drugs, particularly antiarrhythmic, anticoagulant, and plasma lipid lowering chemicals. These substances are also very expensive and the adverse long-term effects of taking them are not known.

A third method has been proposed for treating atherosclerosis. U.S. Pat. No. 4,512,762 describes a photochemical process for destroying atherosclerotic plaques involving the uptake of hematoporphyrin into plaques coupled with lysis of the plaques following irradiation. Unfortunately, this method has two undesirable aspects. First, hematoporphyrin sensitizes patients to subsequent exposure to sunlight. Second, hematoporphyrin is taken up to a significant extent by tissues or cells that surround the plaques. Consequently normal tissue may be destroyed along with the plaques upon subsequent irradiation.

There is a substantial body of literature concerning the treatment of cancer. One regimen, chemical therapy, involves administering drugs to a patient that exert their effects primarily by interrupting DNA synthesis. Such drugs have shown considerable promise and are particularly effective in various combinations when applied to a particular type of cancer. A major drawback associated with chemical therapy, however, is that the therapeutic agent is generally not cell-type specific for cancer cells, but rather is taken up into the DNA of any dividing cell. Consequently, normal cells as well as cancer cells are killed by this treatment. Thus there are severe side effects associated with chemical therapy as it is presently practiced.

One treatment for cancer is described by R. L. Lipson et al., "The Use of a Derivative of Hematoporphyrin in Tumor Detection", *J. Natl. Cancer Inst.*, 26, 1, 1-8, (1961). Hematoporphyrin is injected into a patient experiencing a tumor burden. After injection it is taken up by the tumor. Subsequent irradiation causes lysis of the tumor. Unfortunately, this method has the same drawbacks as treatment of atherosclerosis with hematoporphyrin: the patient may become sensitized to sunlight and there is the likelihood of destruction of normal tissue.

SUMMARY OF THE INVENTION

The present invention provides a new therapeutic method of using a known substance, phycocyanin, that is premised on the photochemical effects of the molecule when it is irradiated with a suitable wavelength of light. In the practice of this invention, phycocyanin is used to destroy malignant tumors. A property of phycocyanin that makes it particularly uniquely suited as an anti-cancer therapeutic agent is that it is selectively taken up in cancer cell membranes, and consequently upon subsequent light or thermal irradiation the target cancer cells are destroyed with little destruction of surrounding normal cells or tissue.

Specifically, the invention is of a method for treating cancer by destroying tumor cells comprising the steps of administering an effective amount of phycocyanin to a patient to effect contact of said phycocyanin with the tumor cells; placing a means for irradiating the tumor cells with light in the area of localization of the tumor cells; and irradiating the tumor cells containing phycocyanin with light from the means for emitting light for a time effective to destroy the tumor cells.

Depending on the type of tumor that is sought to be treated, the mode of treatment wherein phycocyanin is presented to the tumor will vary. For treating skin tumors, phycocyanin can be injected into or about the region of the tumor and followed by subsequent irradiation. For tumors internal to the body, phycocyanin can be presented to the tumor via a catheter and the same catheter can be used to irradiate the tumor. Upon subsequent irradiation with light, phycocyanin undergoes a reaction causing the probable release of a free radical, singlet oxygen. The latter reacts with and is destructive to the cells that comprise the cancerous tumor. Alternatively, phycocyanin is activated by providing a means to selectively absorb laser energy, thereby enhancing thermal ablation of the tumor by laser energy. Irradiation can be provided not only by a catheter containing a suitable light source but also by other methods for irradiating tumors.

DETAILED DESCRIPTION OF THE INVENTION

Figure 1:
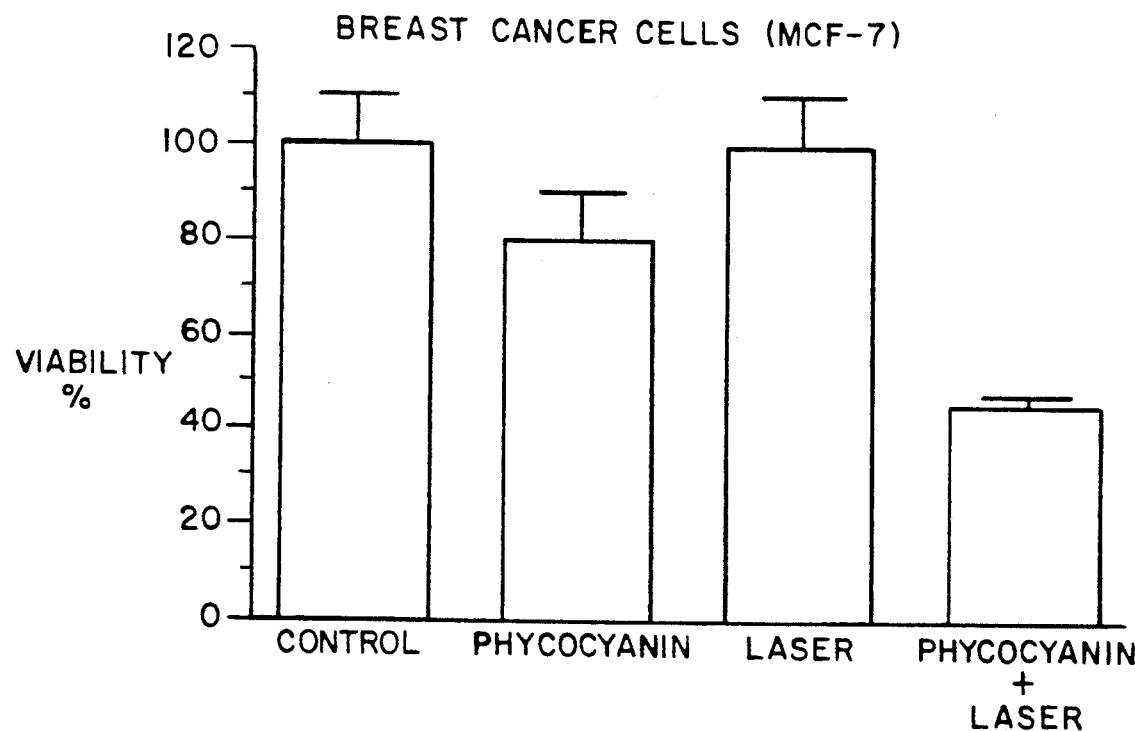
FIG. 1 is a graph illustrating data from comparative experiments on breast cancer cells using phycocyanin, laser therapy or both.

The medical use of phycocyanin in this invention is based either upon the release of singlet oxygen upon irradiation of phycocyanin at a particular wavelength or by the selective absorption of thermal energy. These properties of phycocyanin are particularly suited for the destruction of atherosclerotic plaques and malignant tumors. As noted above, since atherosclerosis treatment and tumor treatment with phycocyanin involves similar considerations and protocols, both aspects of the instant treatment will be described below and will be recognized as being appropriate to the presently claimed invention as well as that described in our aforesaid U.S. Pat. No. 4,886,831.

It will be appreciated that the term phycocyanin refers to a protein-bound pigment having an open-chain tetrapyrrole structural and a blue coloration, which is normally used in solution. Phycocyanin is a member of a broader class of similar compounds termed phycobilins. Because of the similar chemical structures of the members of this group, it is anticipated that a large number of chemical in the group can be substituted for phycocyanin in the instant invention, and the definition of "phycocyanin" is intended to encompass related materials having similar therapeutic properties in this present method. Phycocyanin can be obtained commercially from several sources, one of which is Sigma Chemical Company of St. Louis, Mo.

A favorable property of phycocyanin that enables it to be used successfully to treat tumors is that it appears to be selectively concentrated in the target cancerous cells. Such concentration has been demonstrated with atherosclerotic plaques, using a segment of a human atherosclerotic coronary artery obtained at autopsy treated with 0.1 mg/ml of phycocyanin in a suitable physiologically compatible buffer. Subsequent exposure to monochromatic light at a wavelength of 577 nm (close to the peak absorption of phycocyanin, 620 nm) shows that phycocyanin is predominantly located in the plaque regions and only appears in lesser amounts at the artery walls associated with the thin muscle coat.

As noted, depending on the type of tumor that is sought to be treated, the mode of treatment wherein phycocyanin is presented to the tumor will vary. For treating skin tumors, phycocyanin can be injected subdermally into or about the region of the tumor and followed by subsequent irradiation. For tumors internal to the body, phycocyanin can be presented to the tumor via a catheter and the same catheter can be used to irradiate the tumor or phycocyanin can be injected intravenously, intraperitoneally, intraarterially or intravascularly.

Since tumors are composed of cells which are laden with lipids and other materials, destruction of these cells by photoactivation or thermal absorption of laser energy with phycocyanin should cause destruction of the tumors. As mentioned above, this is thought to be primarily due to singlet oxygen produced by phycocyanin upon irradiation or to thermal ablation. While we do not wish to be bound by this theory, it is, nonetheless, believed that singlet oxygen is at least partially responsible for cellular destruction. Thus the instant invention therefore consists of a method for photodestruction of cancerous tumors by activation of cell-bound phycocyanin.

A variety of procedures are available to effect delivery of light to the desired area and irradiation with light of phycocyanin in tumors. U.S. Pat. Nos. 4,336,809 and 4,512,762 present two conceivably usable methods, and both of these patents are hereby incorporated by reference. The former patent describes a device for delivering laser light of a particular wavelength to a diseased site treated with hematoporphyrin. Hematoporphyrin is known to be cytotoxic to cells when irradiated with a suitable wavelength of light. Thus the system shown in that patent can be beneficially applied to the uses described herein for phycocyanin. U.S. Pat. No. 4,512,762 describes two methods whereby phycocyanin can be delivered and subsequently irradiated to effect treatment at a particular site. The first method is somewhat similar to that of U.S. Pat. No. 4,336,809, in that it involves irradiating hematoporphyrin with a dye laser wherein the light emitted is presented via a balloon catheter to tissue containing hematoporphyrin. A variety of suitable balloon catheters are well known to those skilled in the art. The second method shown in U.S. Pat. No. 4,512,762 is the use of "liquid-light" to effectively irradiate phycocyanin. It is anticipated that there are a variety of chemiluminescent liquids that when injected into the bloodstream of a patient will have few or no side effects, yet will provide sufficient light to irradiate phycocyanin. U.S. Pat. No. 4,512,762 utilizes peroxyoxylate manufactured by American Cyanamid to irradiate hematoporphyrin. It is likely that similar chemicals can be utilized in the instant invention.

It will be appreciated that a major advantage associated with "liquid light" is that it can be injected into the patient without knowing precisely where the tumors reside. That is, once this substance is injected, it will pass throughout the bloodstream, causing it to come into contact with tumors wherever they may have formed. A further advantageous application of this method is that it avoids painful and sometimes dangerous catheterization procedures that are necessarily employed when laser light is delivered via an optical delivery system. Regardless of the type of system used to irradiate phycocyanin, the wavelengths of light suitable for this purpose are in the range of 375 nm, 485–518 nm,, 600 nm, 620 nm or 647 nm. The total energy delivered at these wavelengths can vary depending on the size of the tumor being treated. Of course, it is possible to vary the wavelength and thereby avoid possible adverse heating effects to surrounding tissue arising from prolonged irradiation.

It will be appreciated that virtually any type of tumor can be treated by either method. For instance, both breast cancer and leukemia tumors are effectively treated by the method of this invention, as illustrated by the data shown in FIGS. 1-4. FIGS. 1 and 3 show the percentage of viable cancer cells remaining after twenty hours' in vitro contact with phycocyanin, with equivalent exposure to laser irradiation without phycocyanin being present, and with a combination of phycocyanin and laser irradiation (along with a non-treated control), for breast cancer and leukemia cells respectively. It will be evident that laser irradiation alone is ineffective. Phycocyanin alone, however, is moderately effective in reducing cell viability, while phycocyanin activated by laser irradiation is highly effective on both types of tumors. Other cancer cells show equivalent susceptibility to the phycocyanin and phycocyanin/irradiation treatment, as illustrated by the Examples below, and it is anticipated that many types of tumors not specifically illustrated will also respond to the method of this invention.

It will be further appreciated that phycocyanin is uniquely suited to destroy blood borne metastasis using "liquid light" to effectively irradiate phycocyanin bound to the tumor cells. For instance, phycocyanin in a suitable physiologically compatible solution can be injected into the vascular tree of a patient who is carrying a metastatic tumor whereupon it will contact and bind to any blood borne tumor cells. Upon irradiation by "liquid light", injected along with or after injection of phycocyanin, the metastatic cells will be destroyed.

Figure 2:
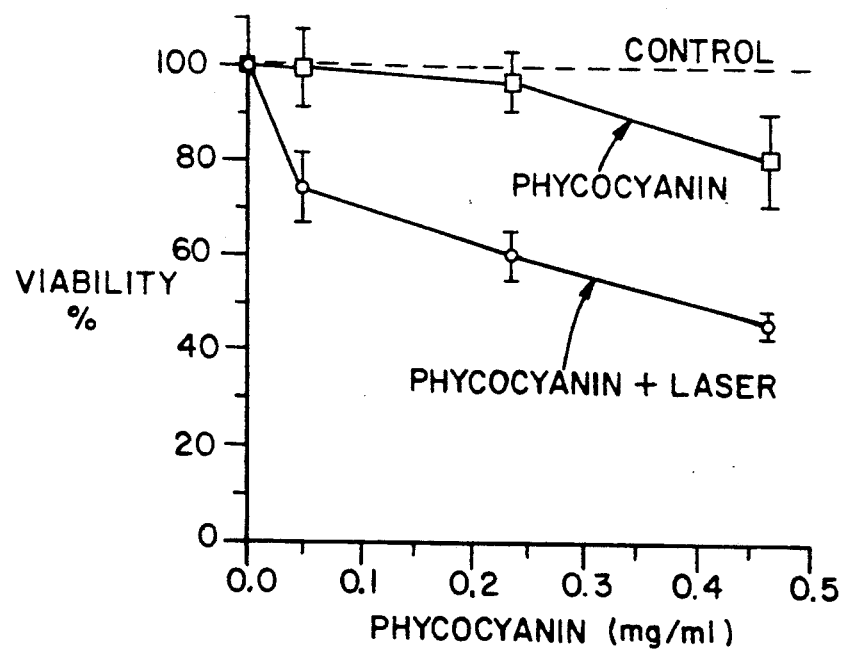
FIG. 2 is a graph from the same series of experiments illustrating the effect of differing concentrations of phycocyanin.
Figure 3:
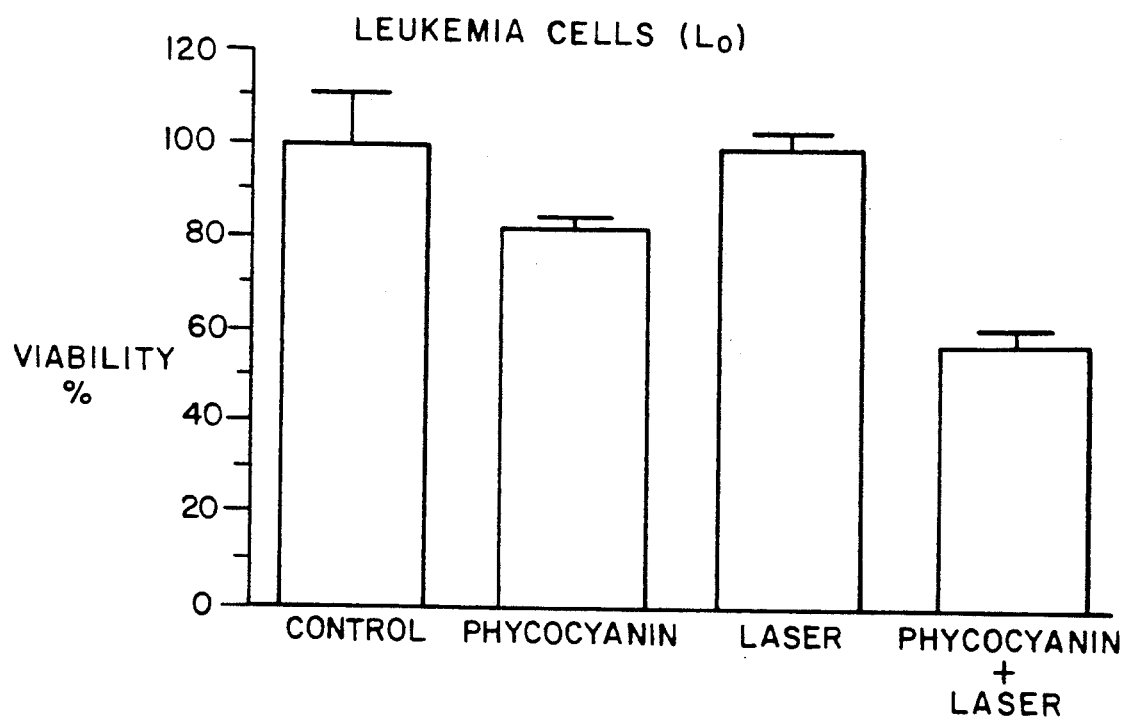
FIGS. 3 and 4 are graphs similar to those of FIGS. 1 and 2 but showing equivalent experiments with leukemia cells.
Figure 4:
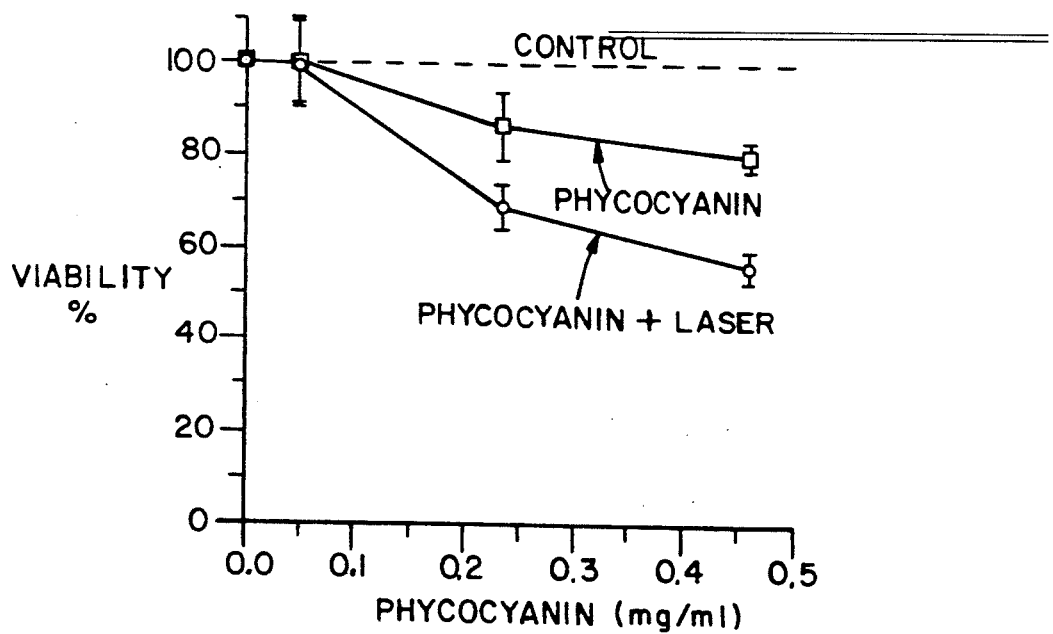

The concentration of phycocyanin will produce optimal effects when applied to the treatment of atherosclerotic plaques or tumors is illustrated in FIGS. 2 and 4, will vary depending on the size, type and location of the disease in the body of the patient. Because the $LD_{50}$ of phycocyanin appears to be 0.3 to 0.5 gm/kg of body weight, a practical dose is less than 0.25 gm/kg of body weight, and a dose of 0.05 gm or less per kg of body weight is likely sufficient. Similarly, it is anticipated that treatment durations of several hours, perhaps 5-10 or more, will be required for full effect. As noted, we have found that twenty hours produced significant decreases in cell viability. Further, we have noted that repetition of treatment causes additional significant reduction in viability. For instance, repeat treatment of the treated cells shown in FIGS. 1-4 can produce essentially 100% reduction in viability after a second phycocyanin/irradiation treatment. For a particular use, the most efficacious concentration and duration of treatment will be determined empirically merely by injecting different concentrations of phycocyanin and subsequently irradiating it for different periods, and then following the course of the patient.

It will be appreciated by those skilled in the art that there are various ways of practicing the instant invention. Thus, the following examples are presented in the spirit of demonstrating representative applications; by no means should they be construed as limiting the invention to these particular applications.

EXAMPLE 1

Effect of Phycocyanin on Experimentally Induced Tumors

An experimentally inducible murine tumor was used as a model system with which to study the effects of phycocyanin irradiation on tumor growth. Several mice were inoculated with a tumorigenic dose using the mouse myeloma cell line Sp2/0. The latter produces dermal tumors in Balb-c mice. After tumors were apparent, phycocyanin was injected intravenously in a balanced saline solution at a concentration of about 0.25 g/kg. Control mice were not injected with phycocyanin, but did receive the saline solution. After 24 hours, both experimental and control mice were irradiated externally with a 15T8 black light florescent bulb for one hour. The latter is produced by Sylvania and emits maximally at 375 nm. Animals which received phycocyanin showed a marked reduction in tumor size within 5 days after light treatment compared to animals which received saline only.

EXAMPLE 2

Elimination of Tumor Growth with Phycocyanin

The materials and methods described in Example 1 were similar here with following exceptions. Five hours after intravenous injection of 0.25 grams of phycocyanin/kg of mouse weight, it was observed that skin covering the tumor exhibited blue coloration indicating that phycocyanin had been concentrated in the tumor. Surrounding normal skin areas were a healthy pink color. Subsequently the tumor was irradiated with an argon laser at wave lengths of 488-518 nm delivered from a cleaved end fiber placed about 5 cm external to the tumor. This generated a 2-cm diameter spot of light. The light adjusted to a total energy dose of about 72 $J/cm^2$. Tumor growth and metastasis was monitored over the following ten day period. This mode of treatment completely inhibited tumor growth during this time. In contrast, animals which were injected with a saline solution lacking phycocyanin, experienced aggressive tumor growth and metastasis during the ten day period.

EXAMPLE 3

Toxicity of Phycocyanin

Studies were done to determine the $LD_{50}$, or the concentration of phycocyanin kills 50% of the mice treated with phycocyanin, using standard techniques well known to those skilled in the art. Approximately 0.3 gm of phycocyanin/kg of body weight was determined to be the $LD_{50}$ when the drug was administered intravenously. Similar studies were conducted on mice which received interperitoneal injections of phycocyanin. The $LD_{50}$ for this route of administration was determined to be about 0.5 gm/kg.

In addition to the above study, the toxicity of phycocyanin to heart tissue was determined. The study consisted of isolating a beating rabbit heart, and perfusing the heart with a suitable saline solution of 64 $\mu M$ phycocyanin for fifteen minutes. There was no effect on the viability of the heart as measured by its contractile properties.

It will be apparent to those skilled in the art that there are various material and method substitutions to the instant invention. Particularly, there are many devices which can be employed for irradiating phycocyanin. The embodiments described above are to be considered in all respects as illustrating but not restricting the scope of the invention. Thus the scope of the invention is indicated by the appended claims rather than by the foregoing Examples, and all changes which come within the meaning and range of equivalency of the claims are therefore intended to be embraced by the claims.

We claim:
1. A method for treating cancer by destroying tumor cells comprising the steps of:
   a. administering an effective amount of phycocyanin to a patient to effect contact of said phycocyanin with said tumor cells;
   b. placing a means for emitting light in the area of localization of said tumor cells; and
   c. irradiating said tumor cells containing said phycocyanin with light from said means for emitting light for a time effective to destroy said tumor cells.
2. A method as in claim 1 for treating cancer by destroying tumor cells wherein said light from said means for emitting light comprises light having a wavelength in the range of 375-647 nm.

3. A method as in claim 2 for treating cancer by destroying tumor cells wherein said light from said means for emitting light comprises light having a wavelength selected from a group consisting of 375, 485-518, 600, 620 and 647 nm.

4. A method as in claim 1 for treating cancer by destroying tumor cells wherein said means for emitting light is a laser.

5. A method as in claim 1 for treating cancer by destroying tumor cells wherein said contact with tumor cells is accomplished by injecting phycocyanin directly into the tumor.

6. A method as in claim 1 for treating cancer by destroying tumor cells wherein said effective amount of phycocyanin for humans is determined by assuming a mouse dosage of less than 0.25 gm/kg of mouse body weight.

7. A method as in claim 6 for treating cancer by destroying tumor cells wherein said effective amount for humans is determined by assuming a mouse dosage of less than 0.05 gm/kg of mouse body weight.

8. A method for treating internal cancer by destroying internally located tumor cells comprising the steps of:
 a. administering an effective amount of phycocyanin internally to a patient to effect contact of said phycocyanin with said tumor cells;
 b. placing a means for emitting light in the area of localization of said tumor cells; and
 c. irradiating said tumor cells containing said phycocyanin with light from said means for emitting light for a time effective to destroy said tumor cells.

9. A method as in claim 8 for treating internal cancer wherein said phycocyanin is administered to said patient by injection means selected from the group consisting of intravenous, intraarterial, intravascular, intraperitoneal, and subdermal injection.

10. A method as in claim 8 for treating internal cancer wherein said phycocyanin is administered to said patient by delivery with a catheter.

11. A method as in claim 8 for treating internal cancer wherein said effective amount of phycocyanin for humans is determined by assuming a mouse dosage of less than 0.25 gm/kg of mouse body weight.

12. A method as in claim 11 for treating internal cancer wherein said effective amount of phycocyanin for humans is determined by assuming a mouse dosage of less than 0.05 gm/kg of mouse body weight.

13. A method as in claim 8 for treating internal cancer wherein said light from said means for emitting light comprises light having wavelengths in the range of 375-647 nm.

14. A method as in claim 13 for treating internal cancer wherein said light from said means for emitting light comprises light having a wavelength selected from a group consisting of 375, 485-518, 600, 620 and 647 nm.

15. A method as in claim 8 for treating internal cancer wherein said means for emitting light is a luminescent chemical placed in proximity to said tumor.

16. A method as in claim 15 for treating internal cancer wherein said luminescent chemical is administered by being injected into said patient.

17. A method for treating skin cancer by destroying tumor cells located on the skin surface comprising the steps of:
 a. contacting said tumor cells with an effective amount of phycocyanin;
 b. irradiating said tumor cells with light from a means for emitting light; and
 c. administering said irradiation for a time effective to destroy said tumor cells.

18. A method as in claim 17 for treating skin cancer wherein said light from said means for emitting light comprises light having wavelengths in the range of 375-647 nm.

19. A method as in claim 18 for treating skin cancer wherein said light from said means for emitting light comprises light having a wavelength selected from a group consisting of 375, 485-518, 600, 620 and 647 nm.

20. A method as in claim 17 for treating skin cancer wherein said means for emitting light is a laser.

21. A method as in claim 17 for treating skin cancer wherein said contact with tumor cells is accomplished by injecting phycocyanin subdermally.

22. A method as in claim 17 for treating skin cancer wherein said contact with tumor cells is accomplished by injecting phycocyanin directly into the tumor.

23. A method as in claim 17 for treating skin cancer wherein said effective amount of phycocyanin for humans is determined by assuming a mouse dosage of less than 0.25 gm/kg of mouse body weight.

24. A method as in claim 23 for treating skin cancer wherein said effective amount for humans is determined by assuming a mouse dosage of less than 0.05 gm/kg of mouse body weight.

* * * * *